US009371387B2

(12) United States Patent
Lee et al.

(10) Patent No.: US 9,371,387 B2
(45) Date of Patent: Jun. 21, 2016

(54) COMPOSITION FOR PREVENTION OR TREATMENT OF ISCHEMIC CARDIAC DISEASE, COMPRISING INHIBITOR AGAINST AGE-ALBUMIN SYNTHESIS OR RELEASE OF MONONUCLEAR PHAGOCYTE SYSTEM CELLS AS ACTIVE INGREDIENT

(71) Applicant: GACHON UNIVERSITY OF INDUSTRY-ACADEMIC COOPERATION FOUNDATION, Gyeonggi-do (KR)

(72) Inventors: Bong Hee Lee, Jeju-do (KR); Kyung Hee Byun, Jeju-do (KR)

(73) Assignee: GACHON UNIVERSITY OF INDUSTRY-ACADEMIC COOPERATION FOUNDATION, Gyeonggi-Do (KR)

( * ) Notice: Subject to any disclaimer, the term of this patent is extended or adjusted under 35 U.S.C. 154(b) by 68 days.

(21) Appl. No.: 14/130,343

(22) PCT Filed: Nov. 12, 2012

(86) PCT No.: PCT/KR2012/009526
§ 371 (c)(1),
(2) Date: Dec. 31, 2013

(87) PCT Pub. No.: WO2013/070048
PCT Pub. Date: May 16, 2013

(65) Prior Publication Data
US 2014/0234343 A1     Aug. 21, 2014

(30) Foreign Application Priority Data
Nov. 10, 2011   (KR) .................. 10-2011-0116914

(51) Int. Cl.
| | |
|---|---|
| *C12N 5/077* | (2010.01) |
| *C12N 5/0786* | (2010.01) |
| *A61K 31/13* | (2006.01) |
| *A61K 31/42* | (2006.01) |
| *A61K 31/138* | (2006.01) |
| *A61K 31/137* | (2006.01) |
| *A61K 31/663* | (2006.01) |
| *A61K 31/545* | (2006.01) |
| *A61K 31/711* | (2006.01) |
| *A61K 31/713* | (2006.01) |
| *A61K 31/4015* | (2006.01) |
| *C07K 16/28* | (2006.01) |
| *G01N 33/50* | (2006.01) |
| *A61K 31/194* | (2006.01) |
| *A61K 31/567* | (2006.01) |
| *A61K 39/00* | (2006.01) |

(52) U.S. Cl.
CPC ............ *C07K 16/2803* (2013.01); *A61K 31/13* (2013.01); *A61K 31/137* (2013.01); *A61K 31/138* (2013.01); *A61K 31/194* (2013.01); *A61K 31/4015* (2013.01); *A61K 31/42* (2013.01); *A61K 31/545* (2013.01); *A61K 31/567* (2013.01); *A61K 31/663* (2013.01); *A61K 31/711* (2013.01); *A61K 31/713* (2013.01); *C12N 5/0645* (2013.01); *C12N 5/0657* (2013.01); *G01N 33/5055* (2013.01); *A61K 2039/505* (2013.01); *C07K 2317/76* (2013.01); *C12N 2500/02* (2013.01); *C12N 2500/38* (2013.01); *C12N 2501/998* (2013.01); *C12N 2501/999* (2013.01)

(58) Field of Classification Search
CPC ............... C12N 5/0657; C12N 5/0645; A61K 31/4015; A61K 31/13; A61K 31/663; A61K 31/138; A61K 31/545; A61K 31/567; A61K 31/194; A61K 31/137; A61K 31/711; A61K 31/42; A61K 31/713
See application file for complete search history.

(56) References Cited

U.S. PATENT DOCUMENTS

| | | | |
|---|---|---|---|
| 5,702,704 A | 12/1997 | Bucala | |
| 6,245,782 B1 * | 6/2001 | Serebruany | ............ A61K 31/00 514/321 |

OTHER PUBLICATIONS

Aleshin, A, et al., "Rage Modulates Myocardial Injury Consequent to LAD Infarction . . . ", Am. J. Physiol. Heart Circ., Physiol 2008, vol. 294, pp. H1823-H1832.
Nakagomi A. et al, "Secondary Preventive Effects of a Calcium Antagonist . . . ", Circulation Journal, May 17, 2011, vol. 75, pp. 1696-1705.
Thomas M. C. et al, The Role of AGE and AGE Inhibitors . . . , Current Drug Targets, 2005, vol. 6, pp. 453-474.
Dukic-Stefanovic S. et al., "Ages in Brain-ageing; AGE-Inhibitors . . . ", Biogerentology, 2001, vol. 2, pp. 19-34, Netherlands.
Bierhuas, A. et al. "Advanced Glycation End Product . . . ", Circulation, circ.ahajournals.org; 1997, vol. 96, 99. 2262-2271.
Sung-Min Ahn et al., "Human Microglial Cells Synthesize Albumin in Brain", Plos One—www.plosone.org, Jul. 2008, vol. 3, 2008, Issue 7 ; e2829.

* cited by examiner

*Primary Examiner* — Daniel C Gamett
(74) *Attorney, Agent, or Firm* — Gottlieb, Rackman & Reisman, P.C.

(57) ABSTRACT

Disclosed is a pharmaceutical composition for the prevention or treatment of ischemic heart diseases, comprising as an active ingredient an inhibitor which acts to restrain mononuclear phagocyte system cells from synthesizing or releasing AGE-albumin, which induces the apoptosis of cardiomyocytes upon the onset of the ischemic heart disease. Also, a method is provided for screening an inhibitor against the AGE-albumin synthesis or release of mononuclear phagocyte system cells. Inhibitory or suppressive of AGE-albumin-induced cell death, the pharmaceutical composition comprising as an active ingredient an inhibitor against the AGE-albumin synthesis or release of mononuclear phagocyte system cells can be applied to the prevention or treatment of a wide spectrum of ischemic heart diseases including myocardial infarction.

8 Claims, 8 Drawing Sheets

COMPOSITION FOR PREVENTION OR TREATMENT OF ISCHEMIC CARDIAC DISEASE, COMPRISING INHIBITOR AGAINST AGE-ALBUMIN SYNTHESIS OR RELEASE OF MONONUCLEAR PHAGOCYTE SYSTEM CELLS AS ACTIVE INGREDIENT

TECHNICAL FIELD

The present invention relates to a composition for the prevention or treatment of an ischemic heart disease, comprising an inhibitor against AGE-albumin synthesis or release of mononuclear phagocyte system cells as an active ingredient. More particularly, the present invention relates to a pharmaceutical composition for the prevention or treatment of an ischemic heart disease, comprising as an active ingredient an inhibitor which suppresses mononuclear phagocyte system cells from synthesizing or releasing AGE-albumin, known to induce the apoptosis of cardiomyocytes at the onset of an ischemic heart disease, and a method for screening the inhibitor.

BACKGROUND ART

Recent studies have revealed that the pathogenesis of various diseases is basically due to abnormal functions of the apoptosis signal transduction system. Apoptosis modulating therapy is designed to control cell growth and death by inducing or suppressing apoptosis, with the aim of fundamentally healing diseases by converting abnormal cells to a normal state as well as halting the progression of diseases by the apoptosis of abnormal cells. Hence, a cell survival-death reversible controlling technology is determined to be the next generation of core technology for apoptosis modulating therapy.

Apoptosis modulating therapy, which is now competitively being developed around the world, can find applications in the treatment of various diseases including leukemia, cancer, Alzheimer's disease, Parkinson's disease, AIDS, senescence and degenerative diseases, and heart diseases. However, apoptosis modulating therapy is arising as a fundamental technique applicable to a wider spectrum of diseases as abnormal functions of the apoptosis signal transduction system are revealed to account for the onset of most diseases.

Configured to either suppress the pathological growth of uncontrollable cells such as cancerous cells or prevent normal cells from undergoing excessive apoptosis as in heart diseases, apoptosis modulating therapy can be used in the therapy of diseases. For cancer, for example, conventional chemotherapy, characterized by causing necrosis over a wide range of cells, not only kills pathological cells, but also exhibits cytotoxicity to normal cells with the concomitant induction of excessive inflammation, as cytotoxic enzymes (e.g., lysozymes) are released upon the lysis of the pathological cells. In contrast, apoptosis modulating therapy induces pathological cells to undergo apoptosis or strongly suppresses the growth of pathological cells without the inflammatory side effects caused by the necrosis of cancer cells. When cells are under the potent power of growth inhibition, cancer cells are more greatly restrained from growing than are normal cells because of the greater proliferative activity of cancer cells. If this inhibitory effect is maximized to induce apoptosis, various cytotoxic intracellular materials are for the most part digested by caspase during apoptosis to lose their functions while being surrounded by apoptotic bodies and subsequently phagocytosed by macrophages. During the phagocytosis, the cytotoxic factors are neither released extracellularly nor exert cytotoxicity on surrounding cells.

Programmed cell death (apoptosis) is active death of cells requiring energy, with the accompaniment of characteristic morphological changes. Given an apoptotic signal, a cell determines to destroy itself and commits suicide. In this phase, the cell undergoes biochemical events which lead to morphological changes. Once apoptosis proceeds, cells shrink and separate from adjacent cells, showing membrane blebbing, chromatic condensation, and chromosomal DNA fragmentation and forming apoptotic bodies that macrophages are able to engulf and quickly remove before the contents of the cell can spill out onto surrounding cells and cause damage. Apoptosis is a complex intracellular process. Although not easily determined, apoptosis may be achieved via various downstream pathways once it is triggered. Caspases, which are aspartic acid specific cysteine proteases, are responsible for most morphological changes which take place during apoptosis.

Within the scope of diseases associated with cell death is ischemic heart disease. Ischemic heart disease is characterized by ischemia to the heart muscle, that is, a significant shortage of oxygen needed for cellular metabolism to keep tissue alive, due to the restriction of blood supply to the heart, resulting in the death of cardiomyoctes and the functional impediment of myocardia. That is, ischemic heart disease may ultimately lead to irreversible injury of the myocardium, i.e., necrosis of cells and tissues. In the early stage of ischemia in which the injury is reversible, it can be prevented from progressing to a fatal degree by reperfusion therapy including surgery, such as percutaneous transluminal coronary angioplasty and coronary artery bypass grafting, and drug therapy, such as thrombolytic therapy. However, even after such reperfusion therapy, there is high incidence of reperfusion injuries such as recurrence of myocardial infarction, cardiac dysfunction, arrhythmia, cognitive impairment, etc. Given ischemia/reperfusion injury, heart diseases, such as myocardial infarction, arrhythmia, cardiac dysfunction, etc., occur with a high prevalence rate and mortality and are difficult to heal. Examples of ischemic heart diseases include coronary artery disease, stable angina, unstable angina, variant angina, myocardial infarction, sudden death, sudden cardiac death, cardiac arrest, heart attack, and the like.

Albumin is a multifunctional protein which is most abundantly found in blood plasma. This plasma protein is produced mainly in the liver and is a major component of most extracellular fluids including interstitial fluid, lymph, and cerebrospinal fluid. Since a reduced level of albumins may lead to hepatic dysfunction and malnutrition, albumin has been extensively used for critical conditions including vascular collapse in serious patients or hepatic cirrhosis patients in clinics. In addition, recent research has suggested that albumin specifically binds to low-molecular weight molecules that might be important diagnostic or prognostic indicators of diseases. For example, albumin is reported to enter the brain across the blood-brain barrier by molecular diffusion and also to be implicated in Alzheimer's disease because it can specifically bind to and transport amyloid beta 1-42 (Aβ1-42). It is also known that albumin can be synthesized in microglial cells, a kind of cell of the mononuclear phagocyte system, in the brain and that the synthesis and extracellular secretion of albumin from microglial cells increases upon microglial activation with Aβ1-42.

Advanced glycation end-products (AGEs) are complex products which are incessantly produced inside the body mainly by reactions between carbohydrates and free amino acids. AGEs are chemically very unstable and reactive and are known as potent molecules that promote neuronal cell death. AGEs are also reported to be found in increased levels in the brain of senile persons or animals, and to exert influence on all cells and biological molecules, causing senescence and senescence-related chronic diseases. That is, AGEs are involved in senescence, Alzheimer's disease, renal disease, diabetes mellitus, diabetic vascular complications, diabetic retinopathy, and diabetic neuropathy, by enhancing vascular permeability, suppressing vasodilation via nitrogen oxide interference, and increasing LDL oxidation, the release of various cytokines from macrophages or endothelial cells, and oxidative stress.

Since AGEs are found, as described above, at an elevated level in the brains of senile persons or animals, and exert influence on most cells, causing senescence and senescence-related chronic diseases, many scientists have suggested that AGEs might have influence on neurodegenerative diseases such as Alzheimer's disease by promoting neuronal cell death. In spite of extensive research results, the precise synthesis mechanism or main secretion places of AGEs still remain unknown. Hence, the discovery of the precise synthesis mechanism and origin of AGEs may be helpful in finding a method for inhibiting the induction of cell death, thus contributing a clue to the etiology of various diseases. There is therefore a need for researching the precise synthesis mechanism of AGEs by which the pathology of various diseases, inter alia, ischemic heart diseases, can be revealed.

DISCLOSURE

Technical Problem

Leading to the present invention, intensive and thorough research into the main synthesis mechanism and origin of AGEs, conducted by the present inventors, resulted in the finding that AGE-albumin is synthesized in and released from macrophages of myocardial infarction, models and induces cardiomyocytes to undergo cell death and that an inhibitor against the AGE-albumin synthesis or release of macrophages is preventive or therapeutic of ischemic heart diseases.

Technical Solution

It is therefore an object of the present invention to provide a pharmaceutical composition for the prevention or treatment of an ischemic heart disease, comprising as an active ingredient an inhibitor against the AGE-albumin synthesis or release of mononuclear phagocyte system cells.

It is another object of the present invention to provide a method for screening the inhibitor.

It is a further object of the present invention to provide a method for treating an ischemic heart disease, using the composition.

Advantageous Effects

Inhibitory or suppressive of AGE-albumin-induced cell death, the pharmaceutical composition in accordance with the present invention comprising as an active ingredient an inhibitor against the AGE-albumin synthesis or release of mononuclear phagocyte system cells can be applied to the prevention or treatment of a wide spectrum of ischemic heart diseases including myocardial infarction.

BEST MODE

In accordance with an aspect thereof, the present invention addresses a pharmaceutical composition for the prevention or treatment of an ischemic heart disease, comprising an inhibitor against the AGE-albumin synthesis or release of mononuclear phagocyte system cells.

As used herein, the term "mononuclear phagocyte system cells" refers to phagocytic cells, which are primarily monocytes, located in reticular connective tissues, and is a generic term for a broad spectrum of cells including macrophages in vivo, monocytes in peripheral blood, and promonocytes and their progenitors in the bone marrow. In the body, mononuclear phagocyte system cells are known to be activated by amyloid beta 1-42 (Aβ1-42), HMGB1, rotenone, 6-hydroxydopamine (6-OHDA), or β2-microglobulin. Examples of the mononuclear phagocyte system cells include brain microglial cells, blood monocytes, alveolar macrophages (type II pneumocytes, dust cells), peritoneal macrophages, granuloma macrophages in inflammation regions, splenic macrophages, Kupffer's cells of the liver, synovial A cells, adventitial cells, macrophages within lymph nodes, and epidermal Langerhans cells, but are not limited thereto. For the purpose of the present invention, the mononuclear phagocyte system cells, a source responsible for the synthesis or release of AGE-albumin, may be the direct target to which the inhibitor is administered or applied.

The term "AGE-albumin," as used herein, refers to a combination of, as implied in the name, albumin and AGE (advanced glycation end-product), which is a complex product which is incessantly produced mainly by reactions between carbohydrates and free amino acids. Since AGEs are causative of neuronal cell death, senescence and senescence-related chronic diseases (e.g., dementia, renal disease, diabetes mellitus, diabetic vascular complications, diabetic retinopathy, and diabetic neuropathy) by enhancing vascular permeability, suppressing vasodilation via nitrogen oxide interference, and increasing LDL oxidation, the release of various cytokines from macrophages or endothelial cells, and oxidative stress, AGE-albumin is acknowledged as having similar actions.

It was first discovered in the present invention that AGE-albumin is preferably synthesized and released by activated mononuclear phagocyte system cells. Briefly, the present inventors revealed that a variety of cytokines, such as SOS cytokine, are synthesized in and released from the cardiomyocytes where mononuclear phagocyte system cells, then gather in response to the cytokines, release various signaling materials including AGE-albumin. When exposed to AGE-albumin, cardiomyocytes increase in RAGE (receptor of AGE) level, and a certain expression level of RAGE triggers a complex pathologic cascade, leading to the ischemic cell death of the cardiomyocytes.

For the purpose of the present invention, therefore, AGE-albumin may be used as a target in preventing or treating ischemic heart diseases such as myocardial infarction.

As used herein, the term "inhibitor against the AGE-albumin synthesis or release of mononuclear phagocyte system cells" refers to a substance that can restrain mononuclear phagocyte system cells from synthesizing or releasing AGE-albumin. The inhibitor may be a biocompatible substance or compound, but is not limited thereto. In this respect, the biocompatible substance may be a peptide or a nucleic acid that regulates a system responsible for the synthesis or release of AGE-albumin in mononuclear phagocyte system cells so as to suppress or reduce the production of AGE, the synthesis of AGE-albumin, or the release of synthesized AGE-albumin. Preferably, the peptidyl or nucletidyl inhibitor preferably include, but is not limited to, a transcription regulatory factor involved in the expression of an albumin gene, an expression inhibitor of albumin gene (e.g., antisense, miRNA, siRNA, etc.), an aptamer, an anti-AGE antibody or a fragment thereof, an anti-albumin antibody or a fragment thereof, and an anti-AGE-albumin antibody or a fragment thereof, with greater preference for a soluble antibody to AGE (sRAGE), or a fragment thereof. As for the inhibitor compound, it may directly or indirectly interfere with a system responsible for the synthesis of release of AGE-albumin in mononuclear phagocyte system cells so as to suppress or reduce the production of AGE, the synthesis of AGE-albumin or the release of synthesized AGE-albumin, and may be derived from a natural source or chemically synthesized.

Preferably, the inhibitor compound may be screened using a method for screening an inhibitor against the AGE-albumin synthesis or release of mononuclear phagocyte system cells inhibitor, comprising: (a) culturing mononuclear phagocyte system cells; (b) incubating the cultured mononuclear phagocyte system cells with (test group) or without (control) a compound candidate; (c) measuring an AGE-albumin level in a lysate or culture medium of the cells incubated in the ischemic condition; and (d) determining the compound candidate as an inhibitor against AGE-albumin synthesis or release when the AGE-albumin level measured in the test group is significantly lower than that in the control. Examples of the inhibitor compound include amantadine hydrochloride, gabaculine hydrochloride, YM 976, acetyl-beta-methylcholine chloride, 5-aminovaleric acid hydrochloride, p-aminoclonidine hydrochloride, azelaic acid, 4-amino-1,8-naphthalimide, (+)-butalclamol hydrochloride, acetohexamide, paroxetine hydrochloride hemihydrates (MW=374.83), cis-4-aminocrotonic acid, Aniracetam, HEMADO, Psora-4, gamma-acetylinic GABA, S(−)-Atenolol, (±)-Baclofen, bupropion hydrochloride, cefaclor, cephalothin sodium, debrisoquin sulfate, phenyloin sodium, N6-cyclohexyladenosine, CK2 inhibitor 2,1,4-dideoxy-1,4-imino-D-arabinitol, N-methyl-1-deoxynojirimycin, 2,4-dinitrophenyl-2-fluoro-2-deoxy-beta-D-glucopyranoside, SANT-1, clodronic acid, emetine dihydrochloride hydrate, edrophonium chloride, ellipticine, Furafylline, fluoxetine hydrochloride, glybenclamide, GW2974, 3-isobutyl-1-methylxanthine, leflunomide, 4-methylpyrazole hydrochloride, BIO, and mifepristone, but are not limited thereto. Also, a pharmaceutically acceptable salt of any one of the compounds may fall within the scope of the inhibitor of the present invention.

The term "pharmaceutically acceptable salt," as used herein, refers to a salt, composed of a cation and an anion with electrical attraction therebetween, which can be used in pharmaceutics. Typically, metal salts, and salts with organic bases, inorganic acids, organic acids, and basic or acidic amino acids may be used. For example, metal salts such as alkali metal salts (sodium salt, potassium salt, etc.), alkaline earth metal salts (calcium salt, magnesium salt, barium salt, etc.), and aluminum salt; salts with organic bases, such as triethylamine, pyridine, picoline, 2,6-lutidine, ethanolamine, diethanolamine, triethanolamine, cyclohexylamine, dicyclohexylamine, and N,N-dibenzylethylenediamine; salts with inorganic acids, such as hydrochloric acid, hydrobromic acid, nitric acid, sulfuric acid, and phosphoric acid; salts with organic acids, such as formic acid, acetic acid, trifluoroacetic acid, phthalic acid, fumaric acid, oxalic acid, tartaric acid, maleic acid, succinic acid, methanesulfonic acid, benzenesulfonic acid, and p-toluenesulfonic acid; salts with basic amino acids, such as arginine, lysine, and ornitine; and salts with acidic amino acids, such as aspartic acid, and glutamic acid may be used.

Preferred examples of salts are inorganic salts such as alkali metal salts (e.g. sodium salts, potassium salts), alkali earth metal salts (e.g. calcium salts, magnesium salts, barium salts), and organic salts such as ammonium salts, when the compound comprises an acidic functional group; and salts with inorganic acids, such as hydrochloric acid, hydrobromic acid, nitric acid, sulfuric acid, and phosphoric acid, and salts with organic acids, such as acetic acid, phthalic acid, fumaric acid, oxalic acid, tartaric acid, maleic acid, citric acid, succinic acid, methanesulfonic acid, and p-toluenesulfonic acid, when the compound comprises an basic functional group The term "ischemic heart disease," as used herein, refers to a disease in which the myocardium is permanently damaged as cardiomyocytes are induced to cell death as a result of the insufficient supply of oxygen and nutrients to the cells. Examples of ischemic heart diseases include coronary artery disease, ischemic heart disease, stable angina, unstable angina, variant angina, myocardial infarction, sudden death, sudden cardiac death, cardiac arrest, and heart attack, but are not limited thereto.

As used herein, the term "prevention" is intended to refer to any action resulting in the suppression or delay of the onset of a certain disease thanks to the administration of the pharmaceutical composition according to the present invention. The term "treatment" is intended to refer to any action resulting in improvements in symptoms of certain diseases or the beneficial alteration of the diseases thanks to the administration of the composition according to the present invention.

Figure 1:
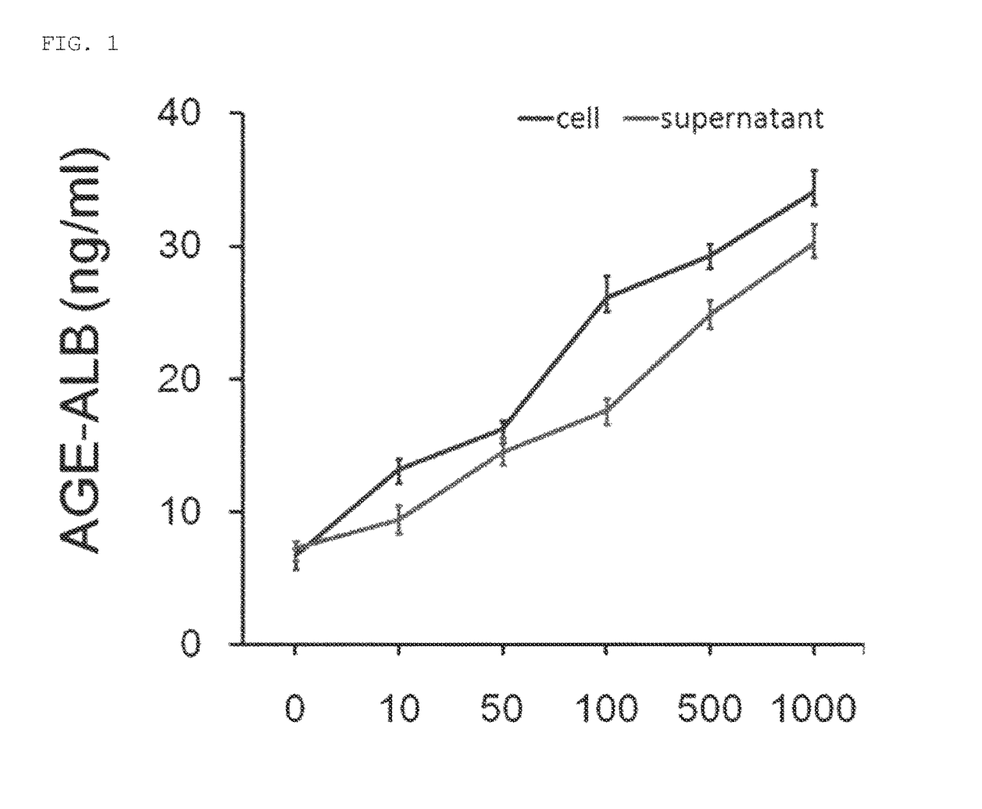
FIG. 1 is a graph in which levels of AGE-albumin synthesized and released by macrophages are plotted versus incubation time.
Figure 2:
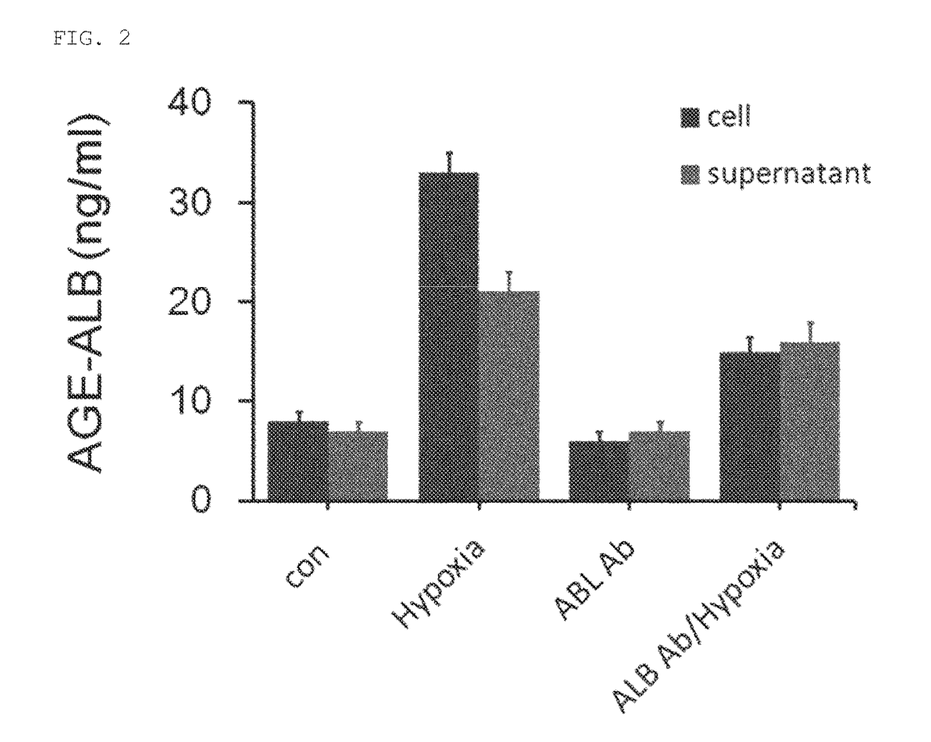
FIG. 2 is a graph showing levels of AGE-albumin synthesized and released by macrophages under various culture conditions.
Figure 3:
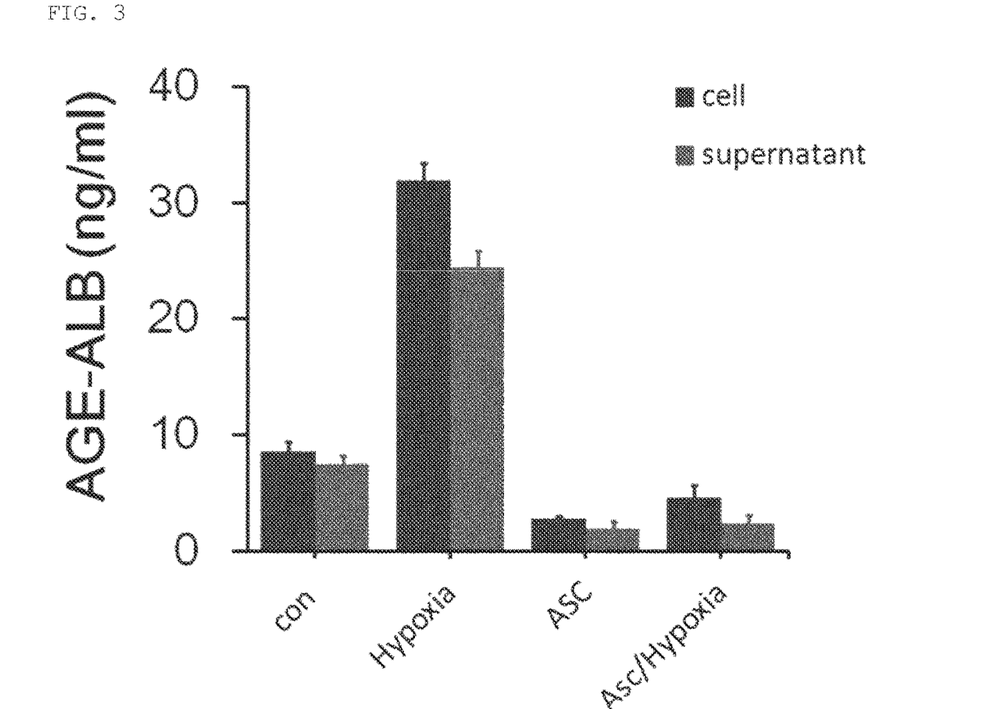
FIG. 3 is a graph showing levels of AGE-albumin synthesized and released by macrophages according to oxidation stress.
Figure 4:
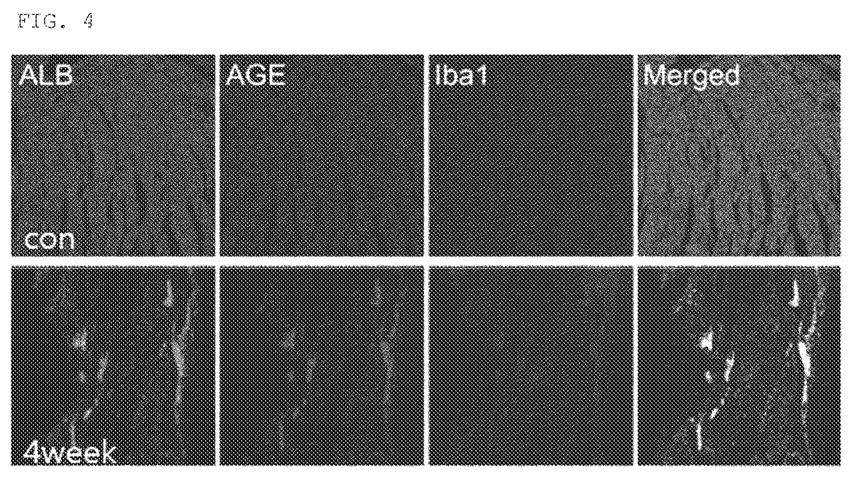
FIG. 4 shows distributions and expression positions of AGE-albumin in heart tissues from normal or myocardial infarction rats (4 weeks old) after staining with antibodies, as observed by a laser confocal fluorescence microscope [AGE (red), albumin (green), and Iba1, a blood monocyte marker (blue)].
Figure 5:
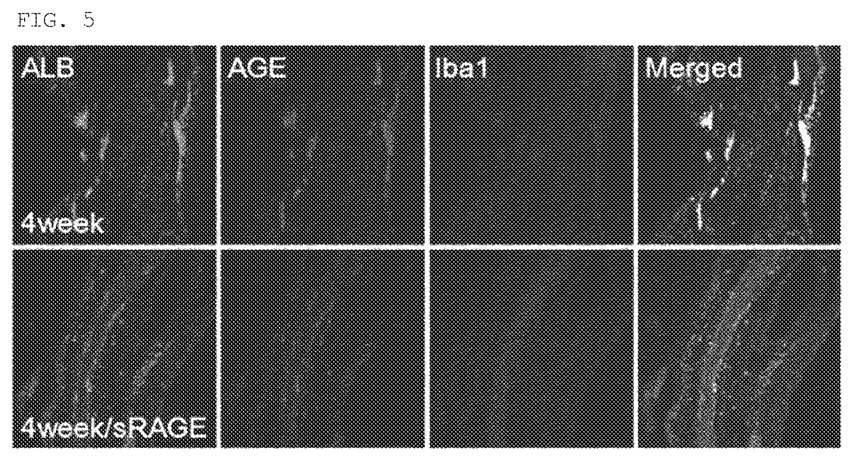
FIG. 5 shows distributions and expression positions of AGE-albumin in heart tissues from myocardial infarction rats treated with or without sRAGE after staining with antibodies to AGE (red), albumin (green) and Iba1, a blood monocyte marker (blue), as observed by a laser confocal fluorescence microscope.
Figure 6A:
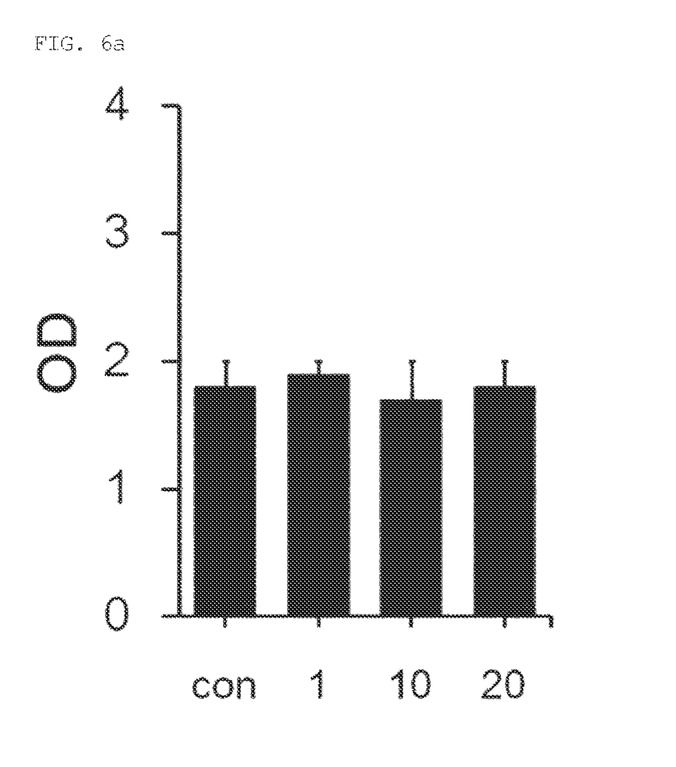
FIG. 6A is a graph of cell viability at various concentrations of albumin applied to cardiomyocytes.
Figure 6B:
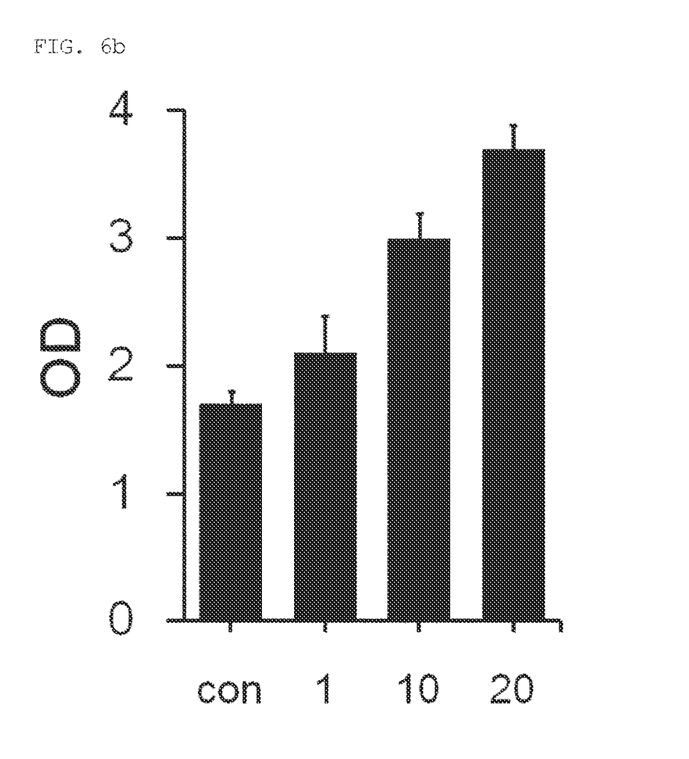
FIG. 6B is a graph of cell viability at various concentrations of AGE-albumin applied to cardiomyocytes.
Figure 7:
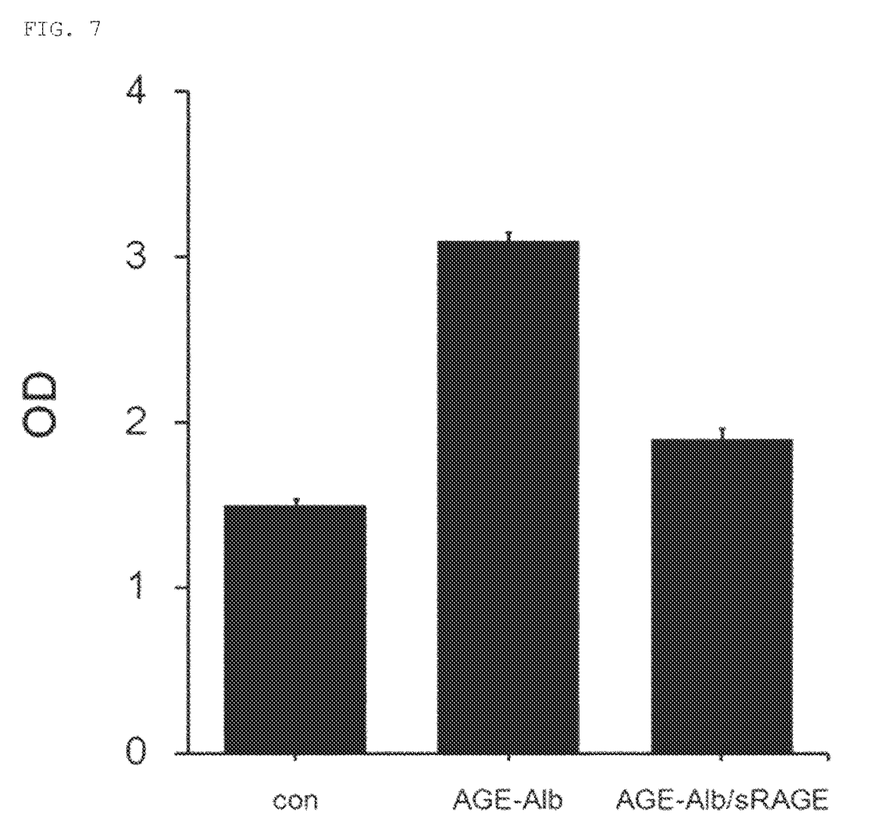
FIG. 7 is a graph showing the protective effect of sRAGE on cardiomyocytes treated with AGE-albumin.
Figure 8:
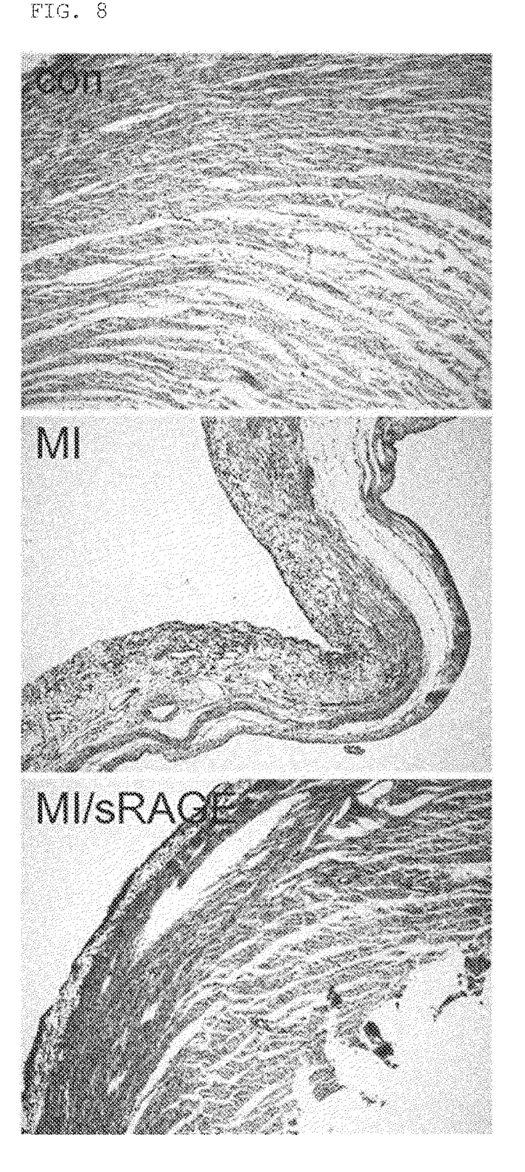
FIG. 8 shows microphotographs taken from cresyl violet-stained heart tissues of myocardial infarction rats which were treated with or without sRAGE.

In one embodiment of the present invention, macrophages, a kind of mononuclear phagocyte system cell, were observed to increase AGE-albumin therein and in the medium in a time-dependent manner when cultured under an ischemic condition (FIG. 1). In addition, even under this ischemic condition, an anti-albumin antibody restrained an increase in AGE-albumin (FIG. 2). Further, when exposed to an oxidative stress, phagocytes increased AGE-albumin therein and in the medium, and exhibited significantly reduced levels of AGE-albumin in the presence of an antioxidant. Thus, oxidative stress induces macrophages to synthesize and release AGE-albumin (FIG. 3). Turning to in vivo tests, blood monocytes, a kind of mononuclear phagocyte system cell, located in the myocardium of rats under hypoxia was observed to express a higher level of AGE-albumin than those located in the myocardium of rats under normoxia (FIG. 4). When the rats with myocardial infarctions were injected with sRAGE, blood monocytes therefrom showed a reduced expression level of AGE-albumin (FIG. 5). Moreover, when exposed to AGE-albumin, cardiomyocytes were induced to decrease in cell viability and to undergo cell death in a dose-dependent manner (FIG. 6). Treatment of the cardiomyocytes with soluble RAGE (sRAGE) prevents AGE-albumin-induced cell death (FIGS. 7 and 8).

Suppressive or reductive of AGE-albumin-induced myocardium cell death, the inhibitor against the AGE-albumin synthesis or release of mononuclear phagocyte system cells or the composition comprising the inhibitor in accordance with the present invention can be applied to the prevention or treatment of ischemic heart diseases led to by an increase in AGE-albumin.

The pharmaceutical composition of the present invention may further comprise pharmaceutically acceptable diluents, vehicles or supporting materials in addition to the inhibitor. The pharmaceutical composition comprising pharmaceutically acceptable supporting materials may be in various oral or non-oral dosage forms. In this regard, the pharmaceutical composition of the present invention may be formulated in combination with a diluent or excipient such as a filler, a thickener, a binder, a wetting agent, a disintegrant, a surfactant, etc. Solid preparations intended for oral administration may be in the form of tablets, pills, powders, granules, capsules, and the like. In regards to these solid agents, the active ingredient of the present invention is formulated in combination with at least one excipient such as starch, calcium carbonate, sucrose, lactose, or gelatin. In addition to a simple excipient, a lubricant such as magnesium stearate, talc, etc. may be used. Among liquid preparations intended for oral administration are suspensions, internal use solutions, emulsion, syrups, and the like. Plus a simple diluent such as water or liquid paraffin, various excipients, such as wetting agents, sweeteners, aromatics, preservatives, and the like may be contained in the liquid preparations. Also, the pharmaceutical composition of the present invention may be in a parenteral dosage form such as sterile aqueous solutions, non-aqueous solvents, suspensions, emulsions, lyophilizates, suppositories, and the like. Injectable propylene glycol, polyethylene glycol, vegetable oils such as olive oil, and esters such as ethyl oleate may be suitable as the non-aqueous solvents and suspensions. The basic materials of suppositories include Witepsol, macrogol, Tween 61, cacao butter, laurin butter, and glycerogelatin.

Further, the form of the dosage of the pharmaceutical composition of the present invention may be selected from the group consisting of a tablet, a pill, a powder, a granule, a capsule, a suspension, an internal use solution, an emulsion, a syrup, a sterile aqueous solution, a non-aqueous solution, a lyophilizate, and a suppository.

In accordance with another aspect thereof, the present invention addresses a method for preventing or treating an ischemic heart disease, comprising administering the composition comprising the inhibitor in a pharmaceutically effective amount to a subject which has been attacked by or is likely to be attacked by an ischemic heart disease.

As used herein, the term "subject" is intended to refer to a living organism in which the onset of an ischemic heart disease is induced. The term "mammalian animal", such as mice, rats, rabbits, dogs, cats, and especially humans, refers to any organism of "the mammal class", which supplies its progeny with milk from the mammary gland.

As mentioned above, the composition may be administered in a pharmaceutically effective amount. The term "therapeutically or pharmaceutically effective amount," as used herein, is intended to refer to an amount of a pharmaceutical composition for treating a disease that is sufficient, at a reasonable benefit/risk ratio applicable to any medical treatment. The level of the effective amount may vary depending on various factors including the severity of the disease being treated, the patient's age and sex, drug activity, sensitivity to the drug, the time of administration, the route of administration, the rate of excretion, the period of time of treatment, the co-administration of drugs, and other parameters well known in the art. The composition of the present invention may be administered as a sole individual agent or in combination with other therapeutics, sequentially or simultaneously. It may be administered in a single dose or it may be spread out over multiple doses per day. In full consideration of these factors, a minimal dose is preferably used as long as it allows for maximum effects.

In accordance with a further object thereof, the present invention addresses a method for inhibiting the induction of cardiomyocytes to undergo cell death, using the inhibitor or the composition. In detail, the method for inhibiting the induction of cardiomyocytes to undergo cell death comprises treating myocardial tissue under an ischemic condition with an inhibitor against the AGE-albumin synthesis and release of mononuclear phagocyte system cells.

In accordance with a still further object thereof, the present invention addresses a method for screening the inhibitor.

The method of screening an inhibitor of AGE-albumin synthesis or release comprises (a) culturing mononuclear phagocyte system cells; (b) incubating the cultured mononuclear phagocyte system cells with (test group) or without (control) a compound candidate; (c) measuring an AGE-albumin level in a lysate or culture medium of the cultured mononuclear phagocyte system cells of the test group or the control; and (d) determining the compound candidate as an inhibitor against AGE-albumin synthesis or release when the AGE-albumin level measured in the test group is significantly lower than that in the control.

In step (b) of the method, the mononuclear phagocyte system cells are preferably incubated under an ischemic condition while step (d) of measuring an AGE-albumin level is preferably performed by ELISA using an anti-AGE antibody or an anti-AGE-albumin antibody in combination with a labeled secondary antibody, or by sandwich ELISA using an anti-AGE antibody or an anti-albumin antibody in combination with a labeled secondary antibody.

Mode for Invention

A better understanding of the present invention may be obtained through the following examples which are set forth to illustrate, but are not to be construed as limiting the present invention.

Example 1

Synthesis and Release of AGE-Albumin in Macrophages of Heart Disease

To examine whether phagocytes, capable of inducing myocardial infarction, synthesize and release AGE-albumin, measurement was made of expression levels of AGE-albumin using ELISA.

Example 1-1

Level of AGE-Albumin Synthesized or Released by Macrophages Cultured Under Ischemic Condition For the in vitro study, immortal human macrophage cells were employed. The macrophages were grown in DMEM (Dulbecco's modified Eagle's medium, Gibco)-high glucose supplemented with 10% heat-inactivated FBS (fetal bovine serum, Gibco) and 20 mg/ml gentamicin (Sigma-Aldrich) at 37° C. in a 5% $CO_2$ atmosphere. Already synthesized albumin was removed from the medium using an anti-albumin antibody before the macrophages were cultured in a hypoxic condition. Intracellular and extracellular (released to the culture medium) levels of AGE-albumin were measured using ELISA.

Briefly, an anti-albumin antibody (Abcam) was diluted to a concentration of 2 ug/ml in a carbonate/bicarbonate buffer and added to each well of 96-well plates (Nunc). After incubation at 4° C. for 12 hrs, the plates were washed three times with 1×PBS to remove the antibody which remained non-immobilized to the well, and then was filled with 5% BSA. An antigen to be measured (cell lysates or culture media) was added in an amount of 30 ug/ml to each well and reacted with the anti-albumin antibody at 37° C. for 90 min. After the plates were washed three time with 1×PBS to remove the antigens which remained unreacted, an anti-AGE antibody (Abcam) was applied at a concentration of 1 ug/ml to each well and incubated at room temperature for 2 hrs. The antibody remaining unreacted was washed off with 1×PBS. Each well was incubated with 1 ug/ml peroxidase-conjugated secondary antibody (Vector laboratory) at room temperature for 2 hrs and washed with 1×PBS to remove the secondary antibodies which remained unreacted. Color was developed with TMB (3,3',5,5'-tetramethylbenzidine) at room temperature for 20 min. When the TMP buffer turned dark blue, the color development was stopped with $2NH_2SO_4$. Absorbance at 450 nm was read on an ELISA reader (VERSA Max, Molecular Devices) (FIG. 1). FIG. 1 is a graph in which levels of AGE-albumin synthesized and released by macrophages are plotted versus incubation time. As is apparent from FIG. 1, intracellular and extracellular (released to the media) AGE-albumin levels increased with time for which the cells were exposed to an ischemic condition.

Example 1-2

Levels of Synthesized or Released AGE-Albumin by Macrophages Under Various Conditions Macrophages were cultured under a normoxic condition without (control) or with an anti-albumin antibody (ABL Ab), or under a hypoxic condition without (Hypoxia) or with an anti-albumin antibody (ABL Ab/Hypoxia). Levels of AGE-albumin in the cells and the culture media were quantified using ELISA (FIG. 2). FIG. 2 is a graph showing levels of AGE-albumin synthesized and released by macrophages under various culture conditions. As can be seen in FIG. 2, a significant increase in the intracellular and extracellular levels of AGE-albumin was detected in the macrophages exposed to a hypoxic condition, compared to those cultured under a normoxic condition. However, the levels of synthesized and released AGE-albumin by the cells were decreased upon treatment with an anti-albumin antibody, but increased upon simultaneous exposure to both an anti-albumin antibody and a hypoxic condition.

Example 2

Increased Synthesis and Release of AGE-Albumin by Oxidative Stress in Human Macrophage Cells Myocardial infarction, representative of ischemic heart diseases, is known to accumulate over a long period of time by oxidative stress. Thus, an examination was made to see whether the synthesis and release of AGE-albumin is directly induced by oxidative stress.

Briefly, macrophages were cultured under a normoxic condition without (con.) or with the antioxidant agent ascorbic acid (ASC) or under 1M hydrogen peroxide ($H_2O_2$), an inducer of oxidative stress, without (Hypoxia) or with ascorbic acid (Asc/Hypoxia), followed by measuring levels of AGE-albumin in the cells and the culture media using ELISA (FIG. 3). FIG. 3 is a graph showing levels of AGE-albumin synthesized and released by macrophages according to oxidation stress. As is apparent from the data of FIG. 3, when macrophages were exposed to hydrogen peroxide, the amount of AGE-albumin was increased in a concentration-dependent manner. In contrast, the addition of the antioxidant ascorbic acid drastically reduced the expression level of AGE-albumin irrespective of hypoxia.

Therefore, the amounts of both intracellular and secreted AGE-albumin in macrophages were observed to positively correlate with the degree of oxidative stress.

Example 3

Distribution and Expression Position of AGE-Albumin in Blood Monocytes of Rats To examine the distribution and expression position of AGE-albumin in blood monocytes of rats, blood monocytes from rats with myocardial infarctions were stained using immunohistochemistry for albumin (green), AGE (red), and DAPI (blue), followed by observation under a laser confocal fluorescence microscope.

Example 3-1

Animal Model

Sprague-Dawley rats, each weighing 250-300 g, were prepared, and anaesthetized with a combination of ketamine (50 mg/kg) and xylazine (4 mg/kg). A 16-gauge catheter was inserted into the bronchus and connected with an artificial respirator. After the animal was fixed with a tape against a flat plate to secure the limbs and the tail, a 1 to 1.5 cm vertical incision was made left from the sternum, and the pectoralis major muscle was separated from the pectoralis minor muscle to ascertain the space between the $5^{th}$ and $6^{th}$ ribs. Then, the muscle therebetween was carefully 1 cm incised in a width-wise direction. A retractor was pushed in between the $5^{th}$ and $6^{th}$ ribs which were then separated further from each other. Since the upper part of the heart is typically covered with the thymus in rats, the thymus was pulled to the head using an angle hook to clearly view the heart. The figure of the left coronary artery was scrutinized to determine the range of artery branches to be tied. The LAD (left anterior descending artery) located 2~3 mm below the junction of the pulmonary conus and the left atrial appendage was ligated with 6-0 silk. Subsequently, the $5^{th}$ and $6^{th}$ ribs were positioned to their original places, and the incised muscle was sutured with MAXON 4-0 filament, followed by withdrawing air from the thoracic cavity through a 23-gauge needle syringe to spread the lungs fully. The skin was sutured with MAXON 4-0 filament. The catheter was withdrawn, and viscous materials were removed from the pharynx. After operation, a pain relieving agent (Buprenorphine 0.025 mg/kg) was subcutaneously injected every 12 hrs.

Example 3-2

Immunohistochemistry (IHC)

Immunohistochemistry was conducted on heart tissues from normal or myocardial infarction rats. Normal or myocardial infarction heart tissues were fixed in 4% paraformaldehyde in a 0.1M neutral phosphate buffer, cryopreserved overnight in a 30% sucrose solution, and then sectioned on a cryostat (Leica CM 1900) at a 10 µm thickness. Paraffin-embedded brain tissues were cut into 4 µm-thick sections, deparaffinized with xylene, and rehydrated with a series of graded ethanol. Normal goat serum (10%) was used to block non-specific protein binding. The tissue sections were incubated overnight at 4° C. with the following primary antibodies: rabbit anti-AGE antibody (Abcam), mouse anti-human albumin antibody (1:200, R&D System), and goat anti-Iba1 antibody (1:500, Abcam). Then, the tissue sections were washed three times with PBS before incubation for 1 hr at room temperature with one of the secondary antibodies: Alexa Fluor 633 anti-mouse IgG (1:500, Invitrogen), Alexa Fluor 488 anti-rabbit IgG (1:500, Invitrogen), and Alexa Fluor 555 anti-goat IgG (1:500, Invitrogen). After washing the secondary antibodies three times with PBS, coverslips were mounted onto glass slides using the Vectashield mounting medium (Vector Laboratories), and observed under a laser confocal fluorescence microscope (LSM-710, Carl Zeiss) (FIG. 4). FIG. 4 shows distributions and expression positions of AGE-albumin in heart tissues from normal or myocardial infarction rats (4 weeks old) after staining with antibodies, as observed by a laser confocal fluorescence microscope [AGE (red), albumin (green), and Iba1, a blood monocyte marker (blue)]. As viewed in FIG. 4, albumin (green) was co-localized with AGE (red) in rat blood monocytes after and before myocardial infarction. In addition, the blood monocytes from myocardial infarction rats were observed to have a wider distribution of albumin and AGE and a higher expression level of AGE-albumin, compared to those from normal rats.

Example 4

Suppression of AGE-Albumin Synthesis in Myocardial Infarction Model (In Vivo) by Soluble RAGE (sRAGE)

To examine the distribution and expression position of AGE-albumin in blood monocytes of rats, rats with myocardial infarctions were administered with sRAGE and blood monocytes from the rats were stained using immunohistochemistry for albumin (green), AGE (red), and DAPI (blue), followed by observation under a laser confocal fluorescence microscope (FIG. 5). FIG. 5 shows distributions and expression positions of AGE-albumin in heart tissues from myocardial infarction rats treated with or without sRAGE after staining with antibodies to AGE (red), albumin (green) and Iba1, a blood monocyte marker (blue), as observed by a laser confocal fluorescence microscope. As viewed in FIG. 5, albumin (green) was co-localized with AGE (red) in rat blood monocytes after and before administration of sRAGE to myocardial infarction rats. A decrease in albumin and AGE was detected in blood monocytes from the myocardial infarction rats administered with sRAGE.

Example 5

Induction of Cell Death by AGE-Albumin in Cardiomyocytes

Stress-activated MAPK (Mitogen-Activated Protein Kinase) is reported to play a critical role in neuronal apoptosis. Hence, experiments were carried out to examine whether AGE-albumin directly induce cell death in human cardiomyocytes, as follows.

Example 5-1

Culturing of Human Cardiomyoctes

Cardiomyocytes were suspended in DMEM (culture medium) containing 5% FBS, 5% HS (horse serum), 20 mg/mL gentamicin and 2.5 mg/mL amphotericin B, plated at a density of $1 \times 10^6$ cells/mL (10 mL) into 10 cm culture dishes, and maintained at 37° C. in a 5% $CO_2$/95% atmosphere in an incubator. After 3 weeks of in vitro culture, the cells were treated with AGE-albumin and used in analyzing apoptosis-related properties.

Example 5-2

Cell Viability (MTT Assay)

Human cardiomyoctes were seeded at a density of $2 \times 10^3$ cells/well into 96-well plates. When reaching 80% confluence, the human cardiomyoctes were treated with various concentrations (0, 1, 10, 20 µg/mL) of albumin or AGE-albumin. After 24 hours of treatment, the cells were rinsed with PBS and examined for viability using an MTT [3-(4,5-dimethylthiazol-2-yl)-2,5-diphenyl tetrazolium bromide] assay. Absorbance in each well was read at 540 nm on a 96-well plate reader (VERSA Max, Molecular Devices) (FIGS. 6A and 6B). FIG. 6A is a graph of cell viability at various concentrations of albumin applied to cardiomyocytes while FIG. 6B is a graph of cell viability at various concentrations of AGE-albumin applied to cardiomyocytes. When human cardiomyocytes were treated with AGE-albumin as illustrated in views in FIGS. 6A and 6B, cell viability decreases with an increase in AGE-albumin concentration, indicating that AGE-albumin induces cell death. In contrast, when human cardiomyocytes were treated with albumin alone, the cell viability remained almost unchanged irrespective of albumin concentration, indicating that albumin does not induce cell death.

Example 6

Protective Effect of Soluble RAGE (sRAGE) on Myocardial Infarction Model Cell Death

Example 6-1

In Vitro Assay

To investigate the protective effect of sRAGE against AGE-albumin-induced cell death, human cardiomyocytes were treated with sRAGE alone, AGE-albumin alone or a combination of sRAGE/AGE-albumin, followed by reading absorbance at 540 nm (FIG. 7). FIG. 7 is a graph showing the protective effect of sRAGE on cardiomyocytes treated with AGE-albumin. As can be seen in FIG. 7, co-treatment with sRAGE and AGE-albumin increased the viability of the human cardiomyocytes, indicating that sRAGE improves resistance to ischemia damage.

Example 6-2

In Vivo Assay

To investigate the protective effect of soluble RAGE (sRAGE) on hypoxia-induced apoptosis of cardiomyocytes, sRAGE was injected into the heart tissue of rats. The relative levels of cardiomyocytes in rat heart tissues were evaluated by cresyl violet staining before microscopy (FIG. 8). FIG. 8 shows microphotographs taken from heart tissues of myocardial infarction rats which were treated with or without sRAGE. As seen in FIG. 8, the relative levels of cardiomyocytes in the heat tissues of myocardial infarction rats treated with sRAGE were dramatically increased.

Hence, sRAGE, a soluble antibody to AGE-albumin, was observed to protect cardiomyocytes from undergoing AGE-albumin-induced cell death.

Example 7

Selection of Candidates for Inhibitor of AGE-Albumin Synthesis

Candidates for inhibitors of AGE-albumin synthesis in macrophages, a kind of mononuclear phagocyte system cells, were selected from among LOPAC (Sigma) compounds as follows.

Macrophages were grown in DMEM (Dulbecco's modified Eagle's medium, Gibco)-high glucose supplemented with 10% heat-inactivated FBS (fetal bovine serum, Gibco) and 20 mg/ml gentamicin (Sigma-Aldrich) at 37° C. in a 5% $CO_2$ atmosphere. Already synthesized albumin was removed from the medium using an anti-albumin antibody, after which the macrophages were treated with 1280 LOPAC (Sigma) compound (5 µM) while being cultured in a condition similar to ischemia. After completion of incubation, the cells were fixed in 100% ethanol and reacted with an AGE-albumin antibody (1:10,000, Abcam) and then with a peroxidase-conjugated secondary antibody (1:5000, Vector). Color was developed with TMB (Sigma), followed by measuring absorbance at 450 nm on an ELISA reader. Selection was made of candidates for an inhibitor of AGE-albumin synthesis in macrophages (Table 1).

TABLE 1

| No. | AGE-Albumin Synthesis Inhibitor Name |
|---|---|
| 1 | Amantadine hydrochloride |
| 2 | Gabaculine hydrochloride |
| 3 | YM 976 |
| 4 | Acetyl-beta-methylcholine chloride |
| 5 | 5-Aminovaleric acid hydrochloride |
| 6 | p-Aminoclonidine hydrochloride |
| 7 | Azelaic acid |
| 8 | 4-Amino-1,8-naphthalimide |
| 9 | (+)-Butalclamol hydrochloride |
| 10 | Acetohexamide |
| 11 | Paroxetine hydrochloride hemihydrate (MW = 374.83) |
| 12 | cis-4-Aminocrotonic acid |
| 13 | Aniracetam |
| 14 | HEMADO |
| 15 | Psora-4 |
| 16 | Gamma-acetylinic GABA |
| 17 | S(−)-Atenolol |
| 18 | (±)-Baclofen |
| 19 | Bupropion hydrochloride |
| 20 | Cefaclor |
| 21 | Cephalothin sodium |
| 22 | Debrisoquin sulfate |
| 23 | Phenytoin sodium |
| 24 | N6-Cyclohexyladenosine |
| 25 | Emetine dihydrochloride hydrate |
| 26 | 1,4-Dideoxy-1,4-imino-D-arabinitol |
| 27 | N-Methyl-1-deoxynojirimycin |
| 28 | Edrophonium chloride |
| 29 | SANT-1 |
| 30 | Clodronic acid |
| 31 | CK2 Inhibitor 2 |
| 32 | 2,4-Dinitrophenyl-2-fluoro-2-deoxy-beta-D-glucopyranoside |
| 33 | Fllipticine |
| 34 | Furafylline |
| 35 | Fluoxetine hydrochloride |
| 36 | Glybenclamide |
| 37 | GW2974 |
| 38 | 3-Isobutyl-1-methylxanthine |
| 39 | Leflunomide |
| 40 | 4-Methylpyrazole hydrochloride |
| 41 | BIO |
| 42 | Mifepristone |

Of the 1280 LOPAC compounds, a total of 42 were selected as candidates for AGE-albumin synthesis inhibitors, as summarized in Table 1.

The invention claimed is:

1. A method for treating an ischemic heart disease, comprising administering, a composition including an inhibitor against AGE (advanced glycation end-product)-albumin synthesis or release of mononuclear phagocyte system cells as an active ingredient, in a pharmaceutically effective amount to a subject which has an ischemic heart disease, wherein the inhibitor is selected from the group consisting of amantadine hydrochloride, gabaculine hydrochloride, YM 976, acetyl-beta-methylcholine chloride, 5-aminovaleric acid hydrochloride, p-aminoclonidine hydrochloride, azelaic acid, 4-amino-1,8-naphthalimide, (+)-butalclamol hydrochloride, acetohexamide, cis-4-aminocrotonic acid, Aniracetam, HEMADO, Psora-4, gamma-acetylinic GABA, (±)-Baclofen, bupropion hydrochloride, cefaclor, cephalothin sodium, debrisoquin sulfate, phenyloin sodium, N6-1-deoxynojirimycin 2,4-dinitrophenyl-2-fluoro-2-deoxy-beta-D-glucopyranoside, SANT-1, clodronic acid, emetine dihydrochloride hydrate, edrophonium chloride, ellipticine, Furafylline, qlybenclamide, GW2974, 3-isobutyl-1-methylxanthine, leflunomide, 4-methylpyrazole hydrochloride, BIO, and mifepristone.

2. The method of claim 1, wherein the mononuclear phagocyte system cells are selected from the group consisting of brain microglial cells, blood monocytes, alveolar macrophages (type II pneumocytes, dust cells), peritoneal macrophages, granuloma macrophages in inflammation regions, splenic macrophages, Kupffer's cells of a liver, synovial A cells, adventitial cells, macrophages within lymph nodes, and epidermal Langerhans cells.

3. The method of claim 1, wherein the ischemic heart disease is selected from the group consisting of coronary artery disease, ischemic heart disease, stable angina, unstable angina, variant angina, myocardial infarction, sudden death, sudden cardiac death, cardiac arrest, and heart attack.

4. The method of claim 1, wherein the composition further comprises a pharmaceutically acceptable diluent, excipient or carrier.

5. A method for screening an inhibitor against the AGE-albumin synthesis or release of mononuclear phagocyte system cells, comprising:
  (a) culturing mononuclear phagocyte system cells;
  (b) incubating the cultured mononuclear phagocyte system cells with (test group) or without (control) a compound candidate;
  (c) measuring an AGE-albumin level in a lysate or culture medium of the cultured mononuclear phagocyte system cells of the test group or the control; and
  (d) determining the compound candidate as an inhibitor against AGE-albumin synthesis or release when the AGE-albumin level measured in the test group is significantly lower than that in the control.

6. The method of claim 5, wherein the mononuclear phagocyte system cells are selected from the group consisting of macrophages, brain microglial cells, blood monocytes, alveolar macrophages (type II pneumocytes, dust cells), peritoneal macrophages, granuloma macrophages in inflammation regions, splenic macrophages, Kupffer's cells of a liver, synovial A cells, adventitial cells, macrophages within lymph nodes, and epidermal Langerhans cells.

7. The method of claim 5, wherein incubating the mononuclear phagocyte system cells in step (b) is performed in an ischemic condition.

8. The method of claim 5, wherein the AGE-albumin level is measured by ELISA using an anti-AGE antibody or an anti-AGE-albumin antibody and with a labeled secondary antibody, or by sandwich ELISA using an anti-AGE antibody, an anti-albumin antibody, and a labeled secondary antibody.

* * * * *